United States Patent [19]

Lang et al.

[11] Patent Number: 5,254,776
[45] Date of Patent: Oct. 19, 1993

[54] SYNTHESIS OF BROMOBIPHENYLS

[75] Inventors: John F. Lang, Webster Groves; Narayanasamy Gurusamy, Ballwin, both of Mo.

[73] Assignee: Mallinckrodt Specialty Chemicals Company, Chesterfield, Mo.

[21] Appl. No.: 916,301

[22] Filed: Jul. 17, 1992

[51] Int. Cl.$^5$ .............................................. C07C 25/18
[52] U.S. Cl. .................................. 570/190; 570/182; 570/183; 570/192
[58] Field of Search ............... 570/184, 185, 190, 199, 570/183

[56] References Cited

U.S. PATENT DOCUMENTS

| | | | |
|---|---|---|---|
| 3,006,972 | 10/1961 | Fields et al. | 570/199 |
| 3,341,569 | 9/1967 | Sharnes | 570/190 |
| 3,401,207 | 9/1968 | Selwitz | 570/190 |
| 3,978,144 | 8/1976 | Eilingsfeld et al. | 570/199 |

OTHER PUBLICATIONS

N. Miyaura et al., The Palladium-Catalyzed Cross--Coupling Reaction of Phenylboronic Acid with Haloarenes in the Presence of Bases, *Synthetic Communications*, 11(7) pp. 513–519 (1981).
R. Miller, et al., Stoichiometric Synthesis of Unsymmetrical Mononitrobiphenyls via the Palladium-Catalyzed Cross-Coupling . . . with Aryl Bromides, *Organometallics*, (3), pp. 1261–1263, (1984).
W. Thompson, et al., A General Synthesis of 5-Arylnicotinates, *J. Org. Chem.*, (49) pp. 5237–5243 (1984).
M. Sharp, et al., Synthetic Connections to the Aromatic Directed Metalation Reaction, *Tetrahedron Letters*, vol. 28, No. 43, pp. 5093–5096 (1987).
Washburn, et al., Preparation, Properties, and Uses of Benzene Boronic Acid, *Metal-Organic Compounds* (ACS Advances in Chemistry Series No. 23), pp. 102–128 (1959).

Primary Examiner—Werren B. Lone
Attorney, Agent, or Firm—Jeffrey S. Boone

[57] ABSTRACT

Bromobiphenyls (such as 2-fluoro-4-bromobiphenyl) are synthesized by reacting together a phenylboronic acid (such as phenylboronic acid) and a bromoiodobenzene (such as 2-fluoro-4-bromoiodobenzene). The reaction generally takes place with the aid of a catalyst (such as palladium in a zero valance state) and an inert solvent (such as fluorobenzene). Control of temperature is very important to obtain both an acceptable reaction rate and an acceptable level of terphenyl byproduct.

22 Claims, No Drawings

SYNTHESIS OF BROMOBIPHENYLS

BACKGROUND OF THE INVENTION

This invention relates to the synthesis of bromobiphenyls. In particular, it relates to such a synthesis from a phenylboronic acid.

Bromobiphenyls are useful intermediates for the production of agricultural chemicals, liquid crystals, and pharmaceuticals. For instance, 2-fluoro-4-bromobiphenyl is the key intermediate for the manufacture of flurbiprofen, a non-steroidal anti-inflammatory and analgesic compound.

N. Miyaura, et. al., The Palladium-Catalyzed Cross-Coupling Reaction of Phenylboronic Acid with Haloarenes in the Presence of Bases, *Synthetic Communications*, 11(7), 513-519 (1981), demonstrated the feasibility of synthesizing unsymmetrical biaryl compounds by the palladium catalyzed coupling of phenylboronic acid with haloarenes. In this reaction, bromobenzene reacted with phenylboronic acid to produce biphenyl in very good yields. Iodobenzene was less reactive, and chlorobenzene was not reactive. A variety of additional reagents such as p-chlorobromobenzene and p-dibromobenzene were also used successfully. The reactions were catalyzed with tetrakis(triphenylphosphine)palladium ($Pd(PPh_3)_4$) and a base. The authors reported that the reaction would not proceed in any noticeable amount in the absence of a base, which was preferably 2 molar aqueous sodium carbonate.

R. Miller, et. al, Stoichiometric Synthesis of Unsymmetrical Mononitrobiphenyls via the Palladium-Catalyzed Cross-Coupling of Arylboronic Acids with Aryl Bromides, *Organometallics*, 1984, 3, 1261-1263, reported the reaction of phenylboronic acid (with and without various methyl substitutions) and o-, m-, and p-nitrobromobenzene to produce nitrobiphenyls. The reaction was also demonstrated with 3-nitrophenylboronic acid and bromoarenes. The general reported reaction scheme used tetrakis(triphenylphosphine)palladium ($Pd(PPh_3)_4$) in the presence of aqueous sodium carbonate solution as the catalyst.

W. Thompson, et. al., A General Synthesis of 5-Arylnicotinates, *J. Org. Chem.*, 1984, 49, 5237-5243; and M. Sharp, Synthetic Connections to the Aromatic Directed Metalation Reaction, *Tetrahedron Letters*. Vol. 28, No. 43, 5093-5096 (1987) both reported reactions and results that also show the reaction of bromobenzenes with phenylboronic acids using tetrakis(triphenylphosphine)palladium ($Pd(PPh_3)_4$) in the presence of a base.

SUMMARY OF THE INVENTION

Briefly, the invention is a method of producing a bromobiphenyl compound comprising reacting a phenylboronic acid with a bromoiodobenzene. The method of the invention allows for the efficient synthesis of bromobiphenyl compounds with a minimum of impurities.

DETAILED DESCRIPTION OF THE INVENTION

In this specification and claims, specific numerical ranges are not critical unless stated otherwise. That is, the numerical ranges should be read as if preceded with the term "about" or "substantially".

One component of the invention is a phenylboronic acid. By "a phenylboronic acid" is meant a compound having a boronic acid moiety, $-B(OH)_2$, attached directly to an aromatic ring. The aromatic ring may be substituted, so long as the substitution does not sterically hinder the coupling reaction, and does not excessively react with the other component. Protective groups may be used to avoid reaction with the other component. In general some of the more complex suitable phenylboronic acids may be prepared by nitration, oxidation, and halogenation of another phenylboronic acid, or by preparation from the corresponding Grignard reagent. Examples of suitable phenylboronic acids include, phenylboronic acid (benzeneboronic acid), o-methylphenylboronic acid, p-methylphenylboronic acid, 2,4,5-trimethylphenylboronic acid, and o-nitrophenylboronic acid. Further information on the synthesis of phenylboronic acids can be found in Washburn, et. al., Preparation, Properties, and Uses of Benzene Boronic Acid, *Metal-Organic Compounds* (ACS Advances in Chemistry Series No. 23), 1959, 102-128; and in the above references, particularly Miller, et. al, and Sharp, et. al.

Another component of the invention is a bromoiodobenzene. By "bromoiodobenzene" is meant an aromatic ring having both a bromine atom and an iodine atom directly on the ring. Other substituants may be on the ring, so long as the substitution does not sterically hinder the coupling reaction, and does not excessively react with the other component. Protective groups may be used to avoid reaction with the other component. In general suitable bromoiodobenzenes include such compounds as unsubstituted bromoiodobenzenes, nitro-substituted bromoiodobenzenes, and bromoiodotoluenes. Specific examples include o-bromoiodobenzene, m-bromoiodobenzene, p-bromoiodobenzene, 2-nitro-4-iodobromobenzene, and 3-nitro-4-iodobromobenzene. The unsubstituted bromoiodobenzenes are the preferred bromoiodobenzenes.

Although some negligible reaction may occur in the absence of a catalyst, a catalyst is necessary for a commercially acceptable reaction rate. Suitable catalysts include those having palladium in a zero valence state. Examples of suitable palladium catalysts include finely divided (precipitated) palladium on an inert support such as carbon, and tetrakis(triphenylphosphine)palladium ($Pd(PPh_3)_4$). Other forms of palladium such as $PdCl_2$, where the palladium is present as $Pd^{++}$, are less effective as a catalyst.

The catalyst should be present in a catalytically effective amount. That is, an amount sufficient to significantly increase the rate of reaction. Generally, the catalyst will be present at 0.05 to 40, desirably 0.1 to 30 and preferably 1 to 20 weight percent, based on the combined weight of the reactants. These amounts, however, may vary considerably depending on such factors as the strength of the catalyst and the dilution of the reaction mixture.

The reaction is generally carried out in the presence of an inert solvent such as fluorobenzene, toluene, or xylene, with fluorobenzene being preferred. A purge of nitrogen or other inert gas is preferred, but not required.

As with many reactions, proper control of temperature is important to maintaining an adequate reaction rate and an adequate product yield. However, in the context of this invention, temperature was also found to have an unexpected influence on the relative reactivity of the bromine and iodine atoms in the bromoiodobenzene. This finding is particularly unexpected in view of the teachings of Miyaura, supra. If the temperature is too low, the reaction rate will be unacceptably slow. However, if the temperature is too high, the phenylboronic acid will react with the desired bromobiphenyl product to form large amounts of undesirable terphenyl byproduct. Although specific reactants and reaction conditions may necessitate some modification, generally the reaction temperature will be 30° to 75°, desirably 40° to 65°, preferably 45° to 60°, and more preferably 50° to 55° C. Proceeding generally in this fashion one obtains a very clean product containing no tar and only small amounts of residual reactants and terphenyl byproduct, both of which may be easily separated from the desired product by distillation. This technique is of broad applicability and can be used to produce a wide variety of bromobiaryl compounds. Although the specific temperature may vary from one reactant to another, a key aspect of obtaining a high yield in the shortest possible reaction time is to identify the highest temperature which will produce an acceptable level of terphenyl impurity. The level of terphenyl which will be considered "acceptable" may vary depending on such factors as equipment available for purification, in general, the level of terphenyl should be less than 20, preferably less than 10, and more preferably less than 5 molar percent, based on the moles of bromoiodobenzene.

EXAMPLE 1

3 g of 2-fluoro-4-bromoiodobenzene, about 0.4 g of PdCl$_2$ and 0.2 g or 5% Pd on carbon, 20 ml of fluorobenzene, and 10 ml of 2M Na$_2$CO$_3$, were added to a 3-neck round bottom flask equipped with a slow nitrogen purge. The mixture was vigorously stirred and 1.21 g of phenylboronic acid in about 5 g of concentrated ethanol was added. The solution was then refluxed at 70°-72° C. The resulting solution was then analyzed by gas chromatography (corrected for sensitivity factors) and it was determined that the desired product, 2-fluoro-4-bromobiphenyl, was produced in 55% yield with about 12% fluoroterphenyl.

EXAMPLE 2

2.13 g (0.0175 mole) of phenylboronic acid, 3.00 g (0.01 mole) of 2-fluoro-4-bromoiodobenzene, 4.00 g (0.042 mole) fluorobenzene, 0.4 g of a palladium on carbon catalyst (5% Pd), and 10 ml of 2M Na$_2$CO$_3$ were placed in a 25-ml round bottom flask (with a nitrogen purge) and heated to 50° C. for 18 hours. Gas chromatography (corrected for sensitivity factors) showed that the desired product, 2-fluoro-4-bromobiphenyl, was produced in 87% yield, with 8% starting material and 3% terphenyl also present. No tar was produced by the reaction. The product was isolated by distillation and characterized by NMR and GC/MS.

EXAMPLE 3

Using conditions essentially identical to those in Example 2, o-iodobromobenzene was used in place of the 2-fluoro-4-bromoiodobenzene to produce 2-bromobiphenyl in 70% yield (by GC analysis).

EXAMPLE 4

Example 3 was repeated using m-iodobromobenzene to produce 3-bromobiphenyl in 70% yield (by GC analysis).

EXAMPLE 5

Example 3 was repeated using p-iodobromobenzene to produce 4-bromobiphenyl in 81% yield (by GC analysis).

EXAMPLE 6

Using methodology generally similar to the above examples, 1.22 g of phenylboronic acid in about 5 ml of ethanol, 3 g of 2-fluoro-4-bromoiodobenzene, 20 g of fluorobenzene, 0.2 g of 5% Pd on carbon catalyst, and 10 ml of 2 molar Na$_2$CO$_3$ were combined and stirred rapidly (without a nitrogen purge) at 25° C. for 65 hours. The desired 2-fluoro-4-bromobiphenyl was produced in about 10% yield with only partial conversion of the starting materials, considerable byproduct formation, but no observed terphenyl formation.

What is claimed is:

1. A method of producing a bromobiphenyl compound comprising reacting together
   a. a phenylboronic acid, and
   b. a bromoiodobenzene.

2. The method of claim 1 wherein said phenylboronic acid is phenylboronic acid, a methylphenylboronic acid, or a nitrophenylboronic acid.

3. The method of claim 2 wherein said phenylboronic acid is phenylboronic acid.

4. The method of claim 1 wherein said bromoiodobenzene is an unsubstituted bromoiodobenzene or a nitro-substituted bromoiodobenzene.

5. The method of claim 4 wherein said bromoiodobenzene is o-, m-, or p-bromoiodobenzene.

6. The method of claim 3 wherein said bromoiodobenzene is o-, m-, or p-bromoiodobenzene.

7. The method of claim 1 wherein said reacting together takes place in the presence of a catalyst.

8. The method of claim 7 wherein said catalyst comprises palladium in a zero valence state.

9. The method of claim 8 wherein said catalyst comprises finely divided palladium on an inert support or tetrakis(triphenylphosphine)palladium (Pd(PPh$_3$)$_4$).

10. The method of claim 9 wherein said catalyst is present at from 0.05 to 40 weight percent, based on the combined weight of the reactants.

11. The method of claim 1 wherein said reacting together takes place in the presence of an inert solvent.

12. The method of claim 11 wherein said inert solvent is fluorobenzene.

13. The method of claim 1 wherein said reacting together takes place at 30° to 75° C.

14. The method of claim 13 wherein said reacting together takes place at 40° to 65° C.

15. The method of claim 13 wherein said reacting together takes place at 45° to 60° C.

16. The method of claim 1 wherein said reacting together takes place at a temperature sufficiently low that less than 20% terphenyl is produced.

17. The method of claim 16 wherein said reacting together takes place at a temperature sufficiently low that less than 10% terphenyl is produced.

18. The method of claim 17 wherein said reacting together takes place at a temperature sufficiently low that less than 5% terphenyl is produced.

19. A method of producing 2-fluoro-4-bromobiphenyl comprising reacting together
   a. phenylboronic acid, and
   b. 2-fluoro-4-bromoiodobenzene in the presence of a catalyst and at a temperature sufficiently low that less than 10% terphenyl is produced.

20. The method of claim 19 wherein said catalyst comprises palladium in a zero valence state.

21. The method of claim 20 wherein said temperature is 45° to 60° C.

22. The method of claim 21 wherein said temperature is sufficiently low that less than 5% terphenyl is produced.

* * * * *